US005686588A

United States Patent [19]

Yoo

[11] Patent Number: 5,686,588
[45] Date of Patent: Nov. 11, 1997

[54] AMINE ACID SALT COMPOUNDS AND PROCESS FOR THE PRODUCTION THEREOF

[76] Inventor: Seo Hong Yoo, 724 tall Oaks Ct., Franklin Lakes, N.J. 07417

[21] Appl. No.: 515,790

[22] Filed: Aug. 16, 1995

[51] Int. Cl.$^6$ .................. C07C 209/00; C07C 209/82; C07C 209/90
[52] U.S. Cl. .................. 536/13.3; 536/13.6; 536/13.8; 536/13.9; 540/220; 540/222; 540/227; 544/114; 544/130; 544/139; 544/162; 544/169; 544/295; 544/360; 544/370; 544/376; 544/392; 544/402; 546/134; 546/271; 549/495
[58] Field of Search .................. 549/495; 546/271, 546/134; 540/220, 222, 227; 536/13.3, 13.6, 13.8, 13.9; 564/497, 391, 512; 544/114, 130, 139, 162, 169, 295, 360, 370, 376, 392, 402; 552/205; 562/560

[56] References Cited

U.S. PATENT DOCUMENTS

| 4,128,658 | 12/1978 | Price et al. | 514/471 |
| 4,399,293 | 8/1983 | Clitherow | 549/494 |
| 4,413,135 | 11/1983 | Clitherow | 549/495 |
| 4,521,431 | 6/1985 | Crookes | 514/47 |
| 4,672,133 | 6/1987 | Crookes | 549/495 |
| 5,221,688 | 6/1993 | Clitherow et al. | 514/400 |
| 5,338,871 | 8/1994 | Ngooi et al. | 549/492 |

FOREIGN PATENT DOCUMENTS

| 2 067 991 | 8/1981 | United Kingdom . |
| 2 160 204 | 12/1985 | United Kingdom . |
| WO90 12002 | 10/1990 | WIPO . |

OTHER PUBLICATIONS

Analytical Profiles of Drug Substances, *Ranitidine*, vol. 15, pp. 533–559, (1986).
*Lange's Handbook of Chemistry*, 14th ed., J.A. Dean, ed., McGraw–Hill, New York, 1992, Table 8.8, § 8.19–8.71.

*Primary Examiner*—Richard L. Raymond
*Attorney, Agent, or Firm*—Kenyon & Kenyon

[57] ABSTRACT

A stoichiometric acid moiety transfer reaction for the preparation of an acid salt of an amine compound is disclosed. The acid moiety transfer reaction provides amine acid salts of high purity and having crystalline structure of uniform size and shape.

46 Claims, 7 Drawing Sheets

AMINE ACID SALT COMPOUNDS AND PROCESS FOR THE PRODUCTION THEREOF

FIELD OF THE INVENTION

This invention relates to amine acid salts and a process for the production and isolation thereof. The present process is a stoichiometric acid moiety transfer reaction (Yoo's Reaction) that provides specific organic amine acid salts in high purity.

BACKGROUND OF THE INVENTION

The acid salts of organic free amines are of particular importance to the pharmaceutical, cosmetic and agrochemical industries since the salt form of organic free amine compounds enables easy storage and handling, particularly of liquids, and improves the chemical and physical stability, pH and solubility of organic free amines in water and other solvents.

The formation of acid salts of organic amines is typically the final step in the process of manufacturing these pharmaceutical raw materials for use in tablets, capsules, pills, granules, powders, cachets, injectable solutions and the like. It is, therefore, critical to eliminate the possibilities of contamination by impurities from side reactions during the production process and degradation and structural transformation of the final product due to excess reaction components. It is also critical to control crystal size and uniformity of the amine acid salts during the production process since crystal size and shape greatly effect stability, hygroscopicity and solubility of the product.

Typically, the processes by which organic amine acid salts are produced include an exothermic neutralization reaction of a strong acid, such as, hydrochloric acid, phosphoric acid, sulfuric acid, nitric acid or acetic acid with the organic free amine or the reaction of an organic acid in solvent with the organic free amine, followed by the addition of an antisolvent to induce crysallization of the organic amine acid salt compound. Alternatively, the solvent may be stripped off to leave the organic amine acid salt compound as residual.

Another process by which organic amine acid salts are produced includes use of solvent in which the organic free amine and acid salt of the organic amine have significantly different solubilities. The exothermic neutralization reaction is carried out in the presence of a strong acid in the solvent.

Each of these processes has serious shortcomings which effect the properties of the organic amine acid salt product. For example, because the exothermic neutralization reaction is a direct reaction between acid and base it is difficult to control the rate of the reaction. Consequently, crystal size and shape cannot be easily controlled.

Moreover, some organic amines are unstable in the acidic conditions required by the exothermic neutralization reaction. It is, therefore, impossible to produce acid salts of these amine compounds by an exothermic neutralization reaction in the presence of strong acid.

Additionally, the use of excess acid in the exothermic neutralization reaction can lead to contamination of the amine acid salt by various side reactions and/or degradation or structural transformation of the final amine salt compound due to the presence of residual acid. Similarly, in the case of amines which have two or more pKa values, the use of excess acid in the neutralization reaction may lead to formation of more than one species of the amine salt, e.g. a mixture of mono-acid and di-acid amine salts, for example.

It is extremely difficult and costly to produce the acid salt equivalent for each pKa of an organic free amine molecule having two or more pKa values and to obtain the hydrate of the acid salt corresponding to each pKa of the organic amine acid salt. Generally, if an organic free amine has more than one pKa, formation of the amine salt by an exothermic neutralization reaction results in complete conversion of the free amine or results in a mixture of mono-, di-, tri-, etc. acid salts or the hydrates of the amine acid salt, depending upon the amount of acid used.

In the exothermic neutralization reaction nucleation occurs immediately upon reaction of a free amine base with a strong acid in solvent, such as ether or ethanol. Consequently, the salt rapidly forms, allowing little or no selectivity in formation of mono-, di-, tri-acid forms of the salt. It is nearly impossible to obtain a pure amine acid salt species that is free from contamination by acid salts having different amounts of acid per organic amine by conventional production methods. This has proven to be problematic, particularly in the pharmaceutical industry, since the amount of acid and corresponding hydrates present on an organic amine acid salt having more than one pKa has a significant effect upon the solubility, stability, pH and hygroscopicity of the amine acid salt.

Many crystalline organic amine salt compounds can exist in more than one polymorphic form, and each polymorph exhibits different thermodynamic properties depending upon its crystalline structure. For example, ranitidine, which is an $H_2$-antagonist, exists as forms I and II, although the production reaction for ranitidine can be biased to provide predominantly one form or the other. However, conventional methods for producing ranitidine and other acid salts of organic amines are severely restricted by the solubility of the organic free amine and its acid salt. Restrictions on solvent selection place serious obstacles in the production of a particular polymorph of organic amine acid salts.

There is, therefore, a need for a process for preparing organic amine salts in pure and highly crystalline form in order to meet pharmaceutical requirements and specifications. Preferably, the process should be operable on an industrial scale. In particular, the process should proceed in a controllable fashion so that the molar amount of acid per mole of free amine can be adjusted to provide the desired number of acid molecules of an amine acid salt and the corresponding hydrate thereof.

In addition, the organic amine acid salt product should be in a form that is readily applicable to final preparation of the compound for pharmaceutical, cosmetic, agrochemical, etc. use.

SUMMARY OF THE INVENTION

In one aspect of the present invention there is provided a novel process for the preparation of an organic amine acid salt compound. It has been found according to the present invention that the rate of the acid moiety transfer reaction and consequently, the size and shape of the resulting amine acid salt crystals and the formation of a particular species of amine acid salt, e.g., mono-, di-, tri-, etc., acid salt of a free amine having more than one pKa may be effected by selection of an amine acid donor compound having a pKa at a desired degree lower than at least the highest pKa of the organic free amine donee compound. It has also been found according to the present invention that the polymorphic form of the resulting organic amine acid salt can be precisely and easily controlled by appropriately adjusting the polarity of the solvent system used to carry out the acid moiety transfer reaction.

Thus, according to the present invention, there is provided a method for preparing an acid salt of an amine compound which comprises placing a donor compound having at least one amine acid salt moiety in solution with a free amine compound, said donor compound having a pKa below at least the highest pKa of the free amine compound, to provide transfer of an acid moiety from the donor compound to the free amine compound yielding as the product thereof an acid salt of the free amine compound. In a preferred embodiment of the invention, the polarity of the protic or aprotic solvent is adjusted to thereby selectively produce a desired polymorph of the crystalline compound.

In another aspect of the invention, there is provided an acid salt product of an amine compound having at least pKa values, wherein said acid salt product is a single species which is substantially free of other species of said acid salt. In a preferred embodiment of the invention, the acid salt product of an amine compound is ranitidine hydrochloride.

In yet another aspect of the invention, there is provided a method of preparing Form I ranitidine hydrochloride which is substantially free of Form II ranitidine hydrochloride comprising treating ranitidine free base with a donor compound capable of transferring HCl to the ranitidine free base in a solvent solution having a polarity suitable for precipitating the Form I ranitidine hydrochloride. In a preferred embodiment of the invention, the Form I ranitidine hydrochloride is a monoacid salt which is substantially free of diacid salt of ranitidine hydrocloride (n>1).

In another aspect of the invention, there is provided a process for removing impurities from a mixture of an amine acid salt compound comprising more than one species of said amine acid salt compound, said process comprising placing said mixture in solution with a free amine compound having a pKa value between two pKa values of the mixture of amine acid salt compound, to provide a selective transfer of acid salt moiety from the amine acid salt compounds comprising said mixture to the free amine to thereby remove impurities from the mixture, yielding as the product thereof a single species of amine acid salt compound.

DETAILED DESCRIPTION OF THE INVENTION

The present invention provides a process for the industrial production of an acid salt of an amine compound having one or more pKa values. The present process is a transfer reaction of acid moiety from an amine acid salt donor or a polymeric amine acid salt donor to free amine as donee of the acid moiety, yielding an acid salt of the free amine compound.

The present process overcomes the many disadvantages and difficulties inherent in processes typically used to produce acid salts of amine compounds. Moreover, the present process provides for the selective formation of a particular species or mixture of species of acid salts of amine compounds. As used herein the term "species" means a particular form of an amine acid salt compound, such as, for example, a mono-acid salt, di-acid salt, etc. or a particular polymorphic structure or hydrate of a crystalline amine acid salt compound.

In the present process, the reaction of an organic free amine (donee) with an amine acid salt compound (donor) in a specified organic solvent system at ambient temperature or elevated temperature may be manipulated to provide for transfer of an acid moiety from the donor compound to a free amine donee compound in an equimolar manner. That is, there is an equimolar amount of acid moieties per each pKa of the donee compound transferred from the amine acid salt donor or polymeric amine acid salt donor to the free amine (donee) based on the difference in pKa between the donor amine and donee amine.

The selection of suitable donor compound for use in the present process may be dependent upon the pKa of the donee compound, the desired species of amine acid salt product and/or the solubility of the donor compound in the reaction solvent. In general, the donor compound may be selected so as to have a pKa of a desired degree lower than at least one pKa of the donee compound (free amine compound) to assure the transfer of an acid moiety to the donee compound. The difference in pKa value between the donor and donee amine compounds may effect the rate of the acid transfer reaction, which in turn effects the size and shape of the amine acid salt crystals that form. The greater the pKa difference between the donor and donee amines, the greater the rate of the reaction. Thus, the rate of the acid transfer reaction can be selectively biased by selecting a donor amine acid salt compound having a desired pKa relative to the pKa of the donee free amine compound.

The donor compound used in the present acid moiety transfer reaction is an organic complex of an amine compound with an acid moiety represented by formula (I):

wherein R, R' and R" are each independently H, an alkyl group having from 1–20 carbon atoms, preferably from one to ten carbon atoms and most preferably, from one to six carbon atoms or an aryl group having from one to nine carbon atoms, and preferably, from one to six carbon atoms or R, R' and R", together with N can form a heterocyclic amine. R, R' and R" may be independently substituted with, for example, an alkyl or aryl group, each having from one to six carbon atoms, a nitrogen, oxygen, silicon, sulfur, or phosphorous group, a halogen atom, an amine group or combinations thereof. (R, R', R")N in Formula (I) is an amine compound, such as, for example, alkylamine, aromatic amine, saturated or unsaturated cyclic amine. $HX^-$ is an acid moiety, such as, for example, hydrochloric acid, sulfuric acid, nitric acid, phosphoric acid or any other mineral acid or organic acid, such as, for example, acetic acid, fumaric acid or maleic acid. Reaction of the organic amine acid salt complex with a free amine compound to transfer an acid moiety to the free amine groups may be achieved in the presence of suitable solvent, however, the amine acid salt complex is not readily dissociated in the solvent.

In general, for selecting an appropriate donor compound the pKa of the donor compound must be lower than at least the highest pKa of the donee free amine compound. The pKa of the donor and donee compounds is based on the basic nitrogens therein. An appropriate donor compound for preparation of a monoacid salt of an amine compound that has two pKa values due to the presence of at least two basic nitrogens would include, for example, those amine compounds having a pKa higher than the lower pKa of the donee compound but lower than the higher pKa of the donee compound, i.e., a pKa value between the two pKa values of the donee compound. Similarly, preparation of a di-acid salt of an amine compound having two pKa values due to basic nitrogens requires a donor compound having a pKa lower than the lower pKa of the donee compound. The preparation of a monoacid salt of a compound that has three pKa values requires a donor compound having a pKa value between the highest pKa value and the second highest pKa value of the donee compound. The di-acid salt of an amine compound having three pKa values is prepared using a donor amine compound having a pKa value between the lowest pKa value and the second highest pKa value of the donee free amine. In preparing the tri-acid salt of an amine compound having three pKa values, the donor compound must have a pKa value below the lowest pKa value of the donee compound. As can be seen from the examples above, a monoacid salt or a selective multi-acid salt of an amine compound can be selectively prepared by utilizing a donor compound having the approprate pKa relative to the pKa(s) of the donee compound. Lange's Handbook of Chemistry, 14th ed., J. A. Dean, ed. McGraw-Hill, New York, N.Y., 1992, Table 8.8, which is incorporated herein in its entirety by reference thereto, discloses the pKa value(s) of a number of organic amine compounds that may be used in the practice of the present acid moiety transfer reaction. Preferred donor compounds used in the practice of the present invention to prepare ranitidine HCl, for example, include pyridine HCl, dimethyl pyridine HCl, chloropyridine and quinoline HCl, and most preferably, 2,5-dimethylpyridine HCl. However, in the preparation of the monoacid salt of ranitidine hydrochloride by the method of the present invention, any amine acid salt having a pKa between 2.3 and 8.2 and which is soluble in the selected solvent may be used.

In addition to its pKa value, the donor compound may also be selected on the basis of its solubility in the solvent or solvents used in the reaction. The donor compound must be soluble in the selected solvent in order for transfer of the acid moiety from the donor amine to donee amine to occur.

Thus, any amine acid salt compound having suitable solubilty in the selected solvent, an appropriate pKa relative to the donee compound and suitable level of nontoxicity may be used in the practice of the present invention.

Thus, unlike conventional methods that are used to prepare amine acid salt compounds, the present method for preparing an acid salt of an amine compound does not rely on neutralization between an acid and base to effectuate formation of the amine acid salt compound. Instead, the important factors in the present method are the difference in amine basicity between the donor compound and donee compound and the solubility of the reaction compounds in the reaction solvent system, which effectuates the transfer of the acid moiety.

While investigation into the mechanisms of the acid moiety transfer reaction are ongoing and Applicant does not wish to be bound by a particular theory or theories, it is believed that the reaction of the donor amine acid compound of formula (I) with the free amine donee compound may be represented by the following general reaction scheme wherein is a free amine compound, R, R' and R" are as defined above and R'", R"", R" are similarly defined. The reaction of the donor amine acid compound of formula (I) with the free amine donee compound is believed to involve a transitory solvation formation between the basic nitrogen(s) of the free amine and the less basic amine of the donor compound, resulting in transfer of an acid moiety from the less basic donor to the free amine compound.

The solvent used in the present process may be selected on the basis of its polarity, solvation and the solubilities therein of the free amine donee compound and the amine acid salt product of the reaction. The donee compound should be soluble in the solvent. However, the solvent should not be a good solvent for the amine acid salt product of the reaction, in that the amine acid salt product should precipitate in the solvent over time. As the amine acid salt product forms the solubilty of this amine acid salt compound in the solvent decreases. As discussed above, it is necessary that the donor amine acid salt be soluble in the selected solvent in order for solvation to occur. For example, it will be readily recognized by those of skill in the art that many free amine compounds are readily soluble in hydroxyl solvent. The selection of donor compound for an acid transfer reaction in hydroxyl solvent, however, will be more limited. A suitable donor compound for use with hydroxyl solvent is 2,5-dimethyl pyridine HCl, for example. Thus, the selection of solvent will depend, in part upon the solubilities and solvation of the reactants and the reaction product.

Solvent may also be selected on the basis of polarity of the solvent and the desired crystalline form of amine acid salt product. It is known that many amine acid salt compounds may have two or more polymorphic structures. For example, ranitidine hydrochloride exists as Form I or Form II. The polarity of the solvent effects the polymorphic form of the crystalline product, therefore, depending upon which polymorph of the product is desired, either a protic or aprotic low polarity solvent or protic or aprotic high polarity solvent may be selected. Protic and aprotic low polarity solvents include, for example, mixtures of tetrahydofuran and ethyl acetate (1:1, v/v) and ethylalcohol and ethyl acetate (1:1, v/v). High polarity solvents include, for example, hydroxyl solvent, such as, ethanol and isopropanol, which are used in the production of ranitidine HCl, for example.

In the present acid moiety transfer reaction nucleation can be made to occur very slowly. If desired, a very long precipitation period may be employed in the production of the amine acid salt product. For example, the precipitation period may be extended from days to weeks. Because nucleation can be made to occur slowly, nucleation in a mixed solvent system generally can be retarded until the solvent mixture is homogeneous. Thus, it is possible to directly effect the polymorphic state of the amine acid salt product of the reaction without the use of strong acid or antisolvent. Consequently, the product of the present acid moiety transfer reaction exhibits increased polymorpic purity in comparison to amine acid salt compounds formed by an exothermic neutralization reaction, for example.

The present stoichiometric acid moiety transfer reaction is driven to completion by the precipitation of amine acid salt product over time. The temperature at which the reaction is carried out can be varied to increase or decrease the rate of the reaction. Generally, the reaction is carried out at a temperature in the range of from about ambient temperature to about 40° C. Preferably, the reaction is carried out at ambient temperature. However, because the acid moiety transfer reaction of this invention is carried out in the absence of free acid or antisolvent, the temperature of the reaction may be elevated without detrimental effect upon the integrity of the product. The temperature of the reaction may be elevated in order to effect the rate of acid moiety transfer reaction and size and shape of the crystalline product without causing any structural transformation of the amine acid salt product by acid hydrolysis or without causing tautomerism of the product. Thus, if desired, the present process can be carried out at elevated temperature of up to about the boiling point of the solvent system.

Crystallization of the amine acid salt product may be assisted by agitation of the reaction mixture during reaction or, if desired, by seeding with appropriate amine acid salt product.

The desired species of amine acid salt compound may be produced by selecting an amine acid salt donor compound having a low pKa relative to that of the pKa(s) of the donee free amine and/or by adjusting the molar amount of reactants. That is, in order to produce a monoacid salt of an amine compound having two or more pKa values due to basic nitrogens, the molar amount of donor amine acid salt used in the reaction is approximately equimolar to the amount of donee free amine in the reaction. Similarly, di-acid amine salts may be produced by the present process by adjusting the molar amounts of donor amine acid salt to donee free amine to about 2:1.

The present acid moiety transfer reaction may be used in the preparation of a wide variety of amine acid salt products. The present process may be used to prepare acid salts of amine compounds such as, for example, ranitidine, to increase the polymorphic and or hydrochloriide salt purity thereof; omeprazole, to produce a mono-hydrochloide salt thereof in the absence of free strong acid; lisinopril, to produce the selected number of acid moities per amine acid salt thereof; diltiazem, to increase the stability and purity thereof; elanapril, to selectively adjust the pH and increase the stability thereof; pirenzepine, to increase the polymorphic purity thereof; melphalan, to increase the solubility thereof; celiprolol, clonidine, mexilene, metoclopranide, terbutaline, terazosin, thiamine, to increase the purity of each of said compounds; antibiotics having one or more basic nitrogens, such as β-lactams, quinolones, cyclopentanoids, macrolides, peptide antibiotics, glycopeptides, carbohydrate antibiotics and the like; cefepime; and the aminoglycoside class of antibiotics, e.g., betamycin, gentamycin, tobramycin, netlimycin and the like. The present process is particularly useful in the production of the acid salts of β-lactam antibiotics since β-lactam antibiotics are unstable in acidic conditions and, therefore, cannot be easily made by conventional methods using an exothermic neutralization reaction and strong acid.

The hygroscopicity, pH, solubility, polymorphic structure and stability of the amine acid salt produced by the process of the present invention may be selectively effected by the adjustment of the amount of acid transferred per free amine donee compound. The amount of acid transferred from the amine acid salt donor compound to the free amine donee molecule may be effected by selection of a donor molecule having a pKa that is a desired degree lower than the pKa of the donee compound. The size and shape of the crystalline form of the amine acid salt compound produced by the present amine acid transfer reaction may be effected by the polarity of the solvent system used in the reaction.

Amine acid salt of a particular compound may be consistently obtained in pure form as a single species that is substantially free of any other structural form of the amine acid salt compound by use of the present process. By "substantially free" of other forms of the compound is meant that no other form, e.g. polymorph or acid salt having a different number of acids on the amine is present in a sample of the compound at an amount sufficient to produce a peak or peaks that may be detected by H-NMR spectroscopy or at an amount sufficient to provide a detectable pattern by X-Ray powder diffraction. The present process also provides amine acid salt compounds of selective size, shape and polymorphic configuration. For example, the present acid moiety transfer reaction provides ranitidine HCl Form I that is substantially free of Form II.

Moreover, because the present process does not require the use of a strong acid or the direct reaction of acid with base, the amine acid salts produced by the present reaction do not undergo structural transformations that may induce change in color or the chemical or physical properties of the compounds. Consequently, the amine acid salt compounds produced by the present acid moiety transfer reaction have significantly improved shelf life in comparison to similar compounds produced by an exothermic neutralization reaction. Additionally, the acid moiety transfer reaction of the present invention provides amine acid salt compounds of significantly improved purity due, in part, to the elimination of acid which is known to induce side reactions resulting in impurities, and the ability to selectively effect the rate of the acid transfer.

The process of the present invention provides ranitidine hydrochloride having significantly improved purity in comparison to ranitidine hydrochloride prepared by other known methods. When ranitidine hydrochloride is prepared by an exothermic neutralization reaction as described in U.S. Pat. No. 4,128,658 it is subject to structural transformation due to the presence of excess acid or strong acid (HCl). Structural transformation of the amine may induce color change, alteration of chemical and physical properties of the compound and the formation of hazardous impurities, all of which may effect the shelf life and/or therapeutic effectiveness of the compound.

Moreover, preparation of ranitidine hydrochloride by the process of U.S. Pat. No. 4,128,658 provides Form I ranitidine hydrochloride that is contaminated by Form II, which is formed at the time the acid salts begin to crystallize. Crystallization begins as soon as ranitidine free base is added to the alcohol-HCl solution, even before the addition of antisolvent.

Additionally, the use of excess hydrogen chloride in the neutralization reaction results in the production of ranitidine n HCl (n>1), which consists of one mole of ranitidine free base and more than one mole of hydrogen chloride. Ranitidine n HCl (n>1) is extremely hygroscopic and acidic and has very poor solubility in organic solvent. Thus, ranitidine n HCl (n>1) cannot exist in crystalline form in the atmosphere or as a mixture with Form I or Form II ranitidine hydrochloride because of its hygrosopicity. Because of the poor solubility of ranitidine hydrochloride n HCl (n>1) in organic solvent it is extremely difficult to remove this contaminant from the desired product. For example, when ranitidine n HCl (n=1) is contaminated by a very small amount of ranitidine n HCl (n>1), the mixture becomes acidic because the contaminant ranitidine n HCl (n>1) rapidly absorbs moisture from the atmosphere. When ranitidine n HCl (n=1) is contaminated with ranitidine n HCl (n>1) the contaminant accelerates the degradation and/or color change of ranitidine hydrochloride in the atmosphere.

Figure 3:
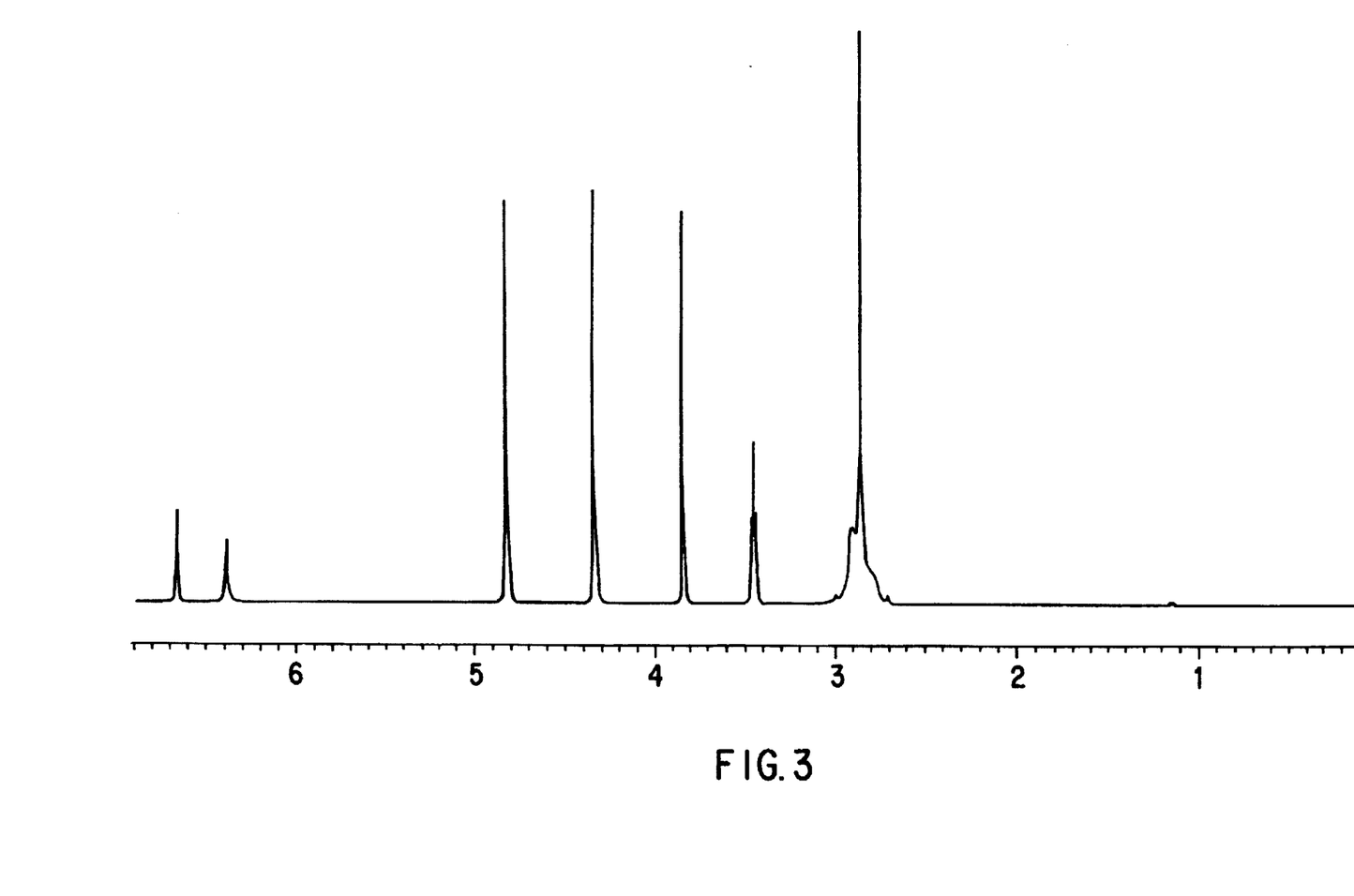
FIG. 3 is an H-NMR spectrum of ranitidine n HCl (n=1) in $D_2O$ prepared by the process of the present invention.
Figure 4:
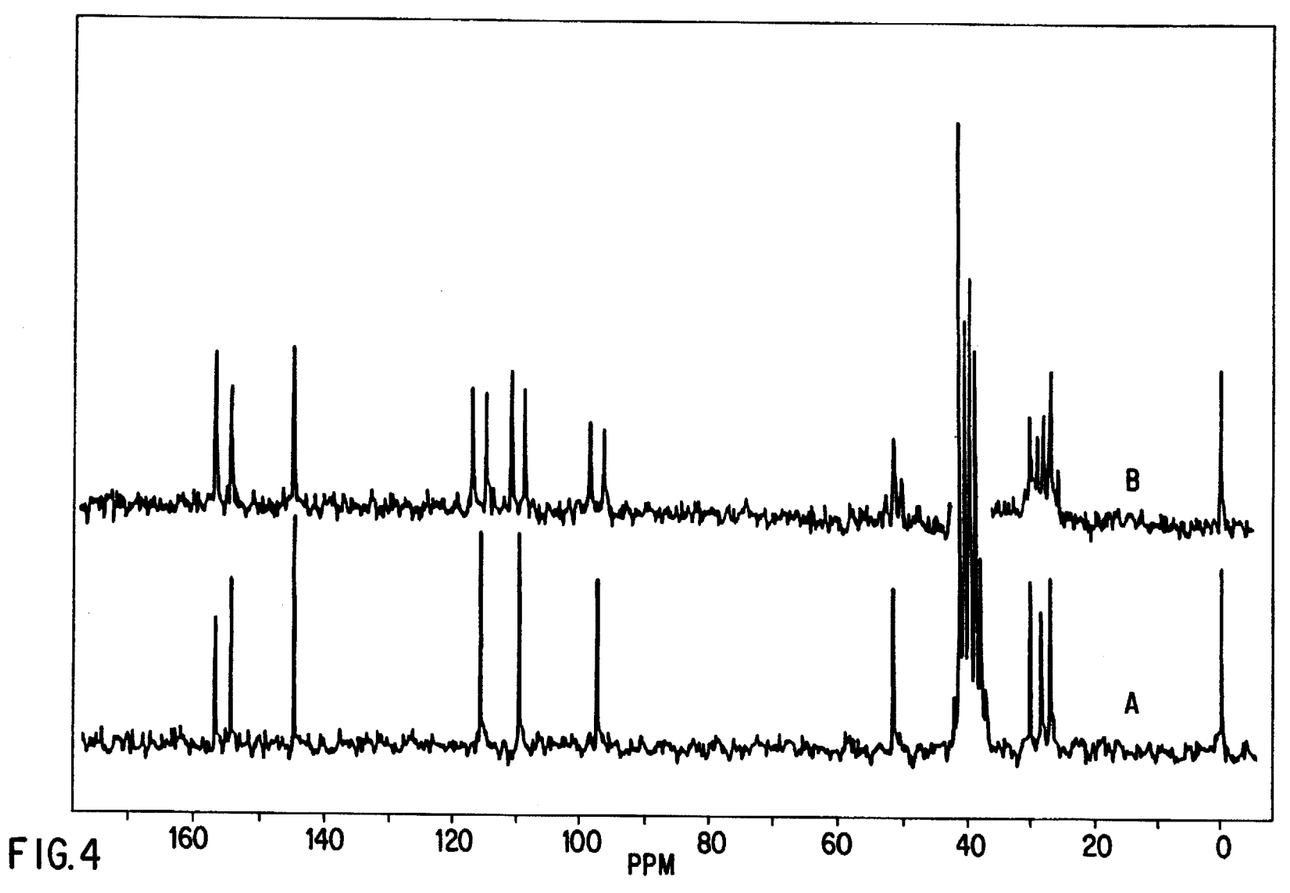
FIG. 4 is a published $^{13}$C-NMR spectrum of ranitidine n HCl (n=1) (Analytical Profiles of Drug Substances, "Ranitidine", Hohnjec, et al., vol. 15, 1986, p. 533–559.
Figure 5:
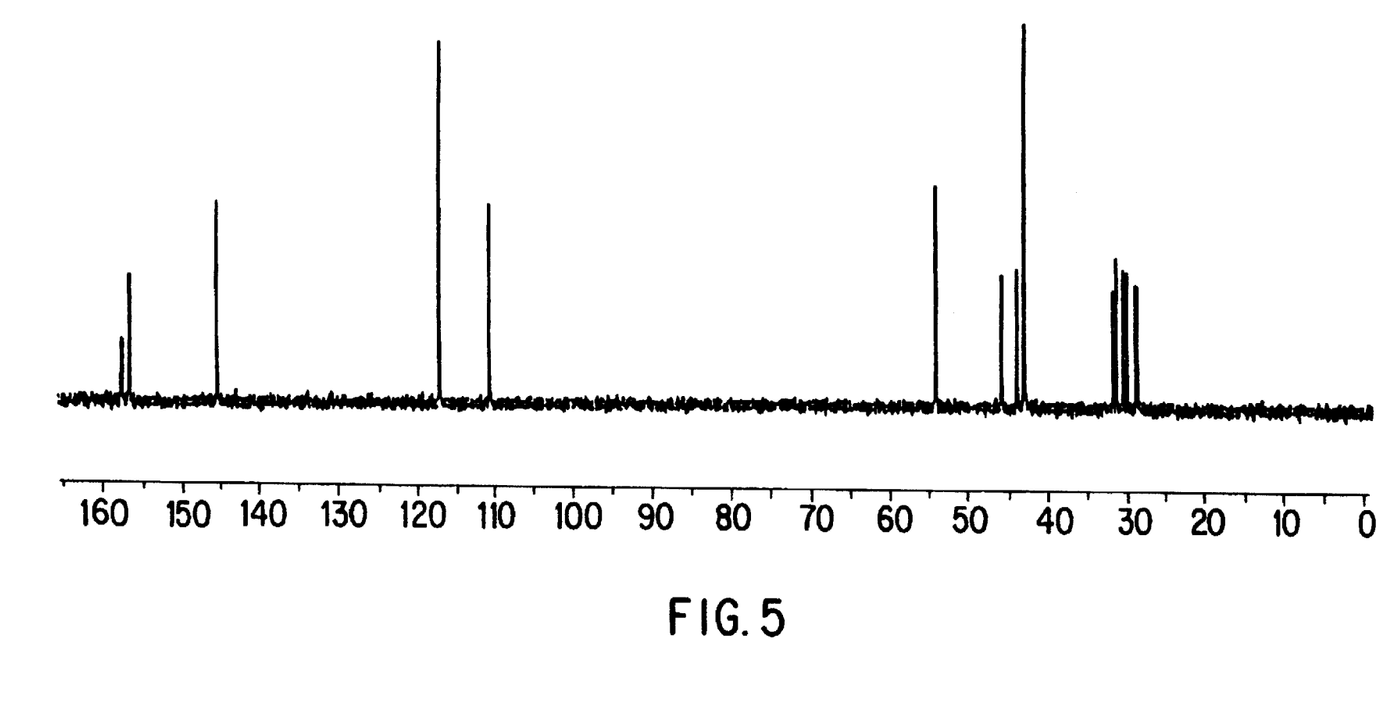
FIG. 5 is a $^{13}$C-NMR spectrum of ranitidine n HCl (n>1) in $CD_3OD$ prepared by a conventional exothermic neutralization reaction using hydrogen chloride.
Figure 6:
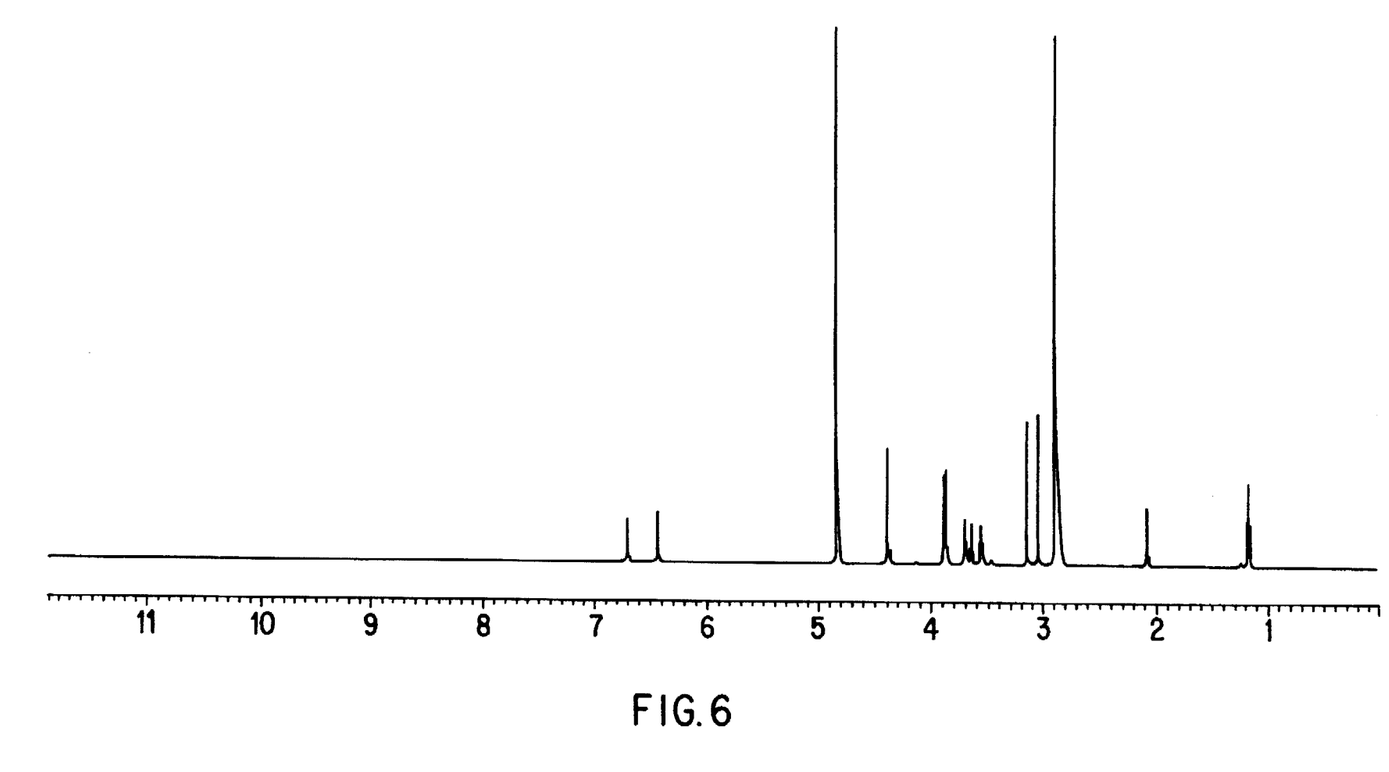
FIG. 6 is an H-NMR spectrum of ranitidine n HCl (n>1) in $D_2O$ prepared by a conventional exothermic neutralization reaction using hydrogen chloride.

FIG. 6 provides an H-NMR spectrum of ranitidine n HCl (n>1) prepared by a conventional neutralization reaction using strong acid. The H-NMR spectrum of the monoacid salt form of ranitidine n HCl (n=1) prepared by the present method is shown in FIG. 3. As can be seen, the existence of ranitidine n HCl (n>1) can be readily detected by H-NMR spectroscopy by the presence of two peaks between the peaks at about 3.9 and about 3.5 PPM and two peaks between about 3.4 and about 2.9 PPM. The H-NMR spectrum of the monoacid form of ranitidine n HCl (n=1) does not have these four peaks. All other characteristic features of ranitidine n HCl (n=1) produced by the present method are the same as disclosed in Analytical Profile of Drug Substance, vol. 15, 1986, incorporated herein by reference.

Ranitidine hydrochloride produced by the present stoichiometric acid moiety transfer reaction is substantially free of contamination by ranitidine n HCl (n>1) and Form II ranitidine HCl. Consequently, ranitidine hydrochloride of the present invention is less hygroscopic, more stable to the atmosphere and light and the crystals are of uniform size and shape.

The present acid moiety transfer reaction can also be used to purify a desired amine acid salt species from a mixture of more than one species of the amine acid salt. Removal of impurities from a mixture of an amine acid salt containing more than one species of the amine acid salt is achieved by placing the mixture in solution with a free amine compound having a pKa value between two pKa values of the mixture of the amine acid salt compound, which results in the selective transfer of acid moiety from the impurities to the free amine. This reaction yields, as the product, a single species of the amine acid salt compound. In a preferred embodiment of the invention, the process is used to purify a single species of ranitidine hydrochloride from a mixture of ranitidine hydrocloride containing more than one species thereof.

In order that the invention may be more fully understood the following examples are given by way of illustration only and are meant in no way to be limiting.

EXAMPLE 1

Preparation of Form I ranitidine hydrochloride

Ranitidine free base (50 g, 0.16 mol) was dissolved in 500 ml of a mixture of industrial methylated spirits (250 ml, 74° o.p.) and ethylacetate (250 ml). 24.13 g (0.168 mol) of 2,5-dimethylpyridine hydrochloride was added to the reaction mixture with stirring and under protection from atmospheric moisture. Ranitidine hydrochloride was allowed to crystallize with stirring. The crystals were filtered off, washed with a mixture of industrial methylated spirits (25 ml) and ethylacetate (25 ml) and dried at 50° C. under reduced pressure to give 50 g of Form I ranitidine hydrochloride, which was free from contamination from Form II ranitidine n hydrochloride (n>1) and other impurities.

Figure 1:
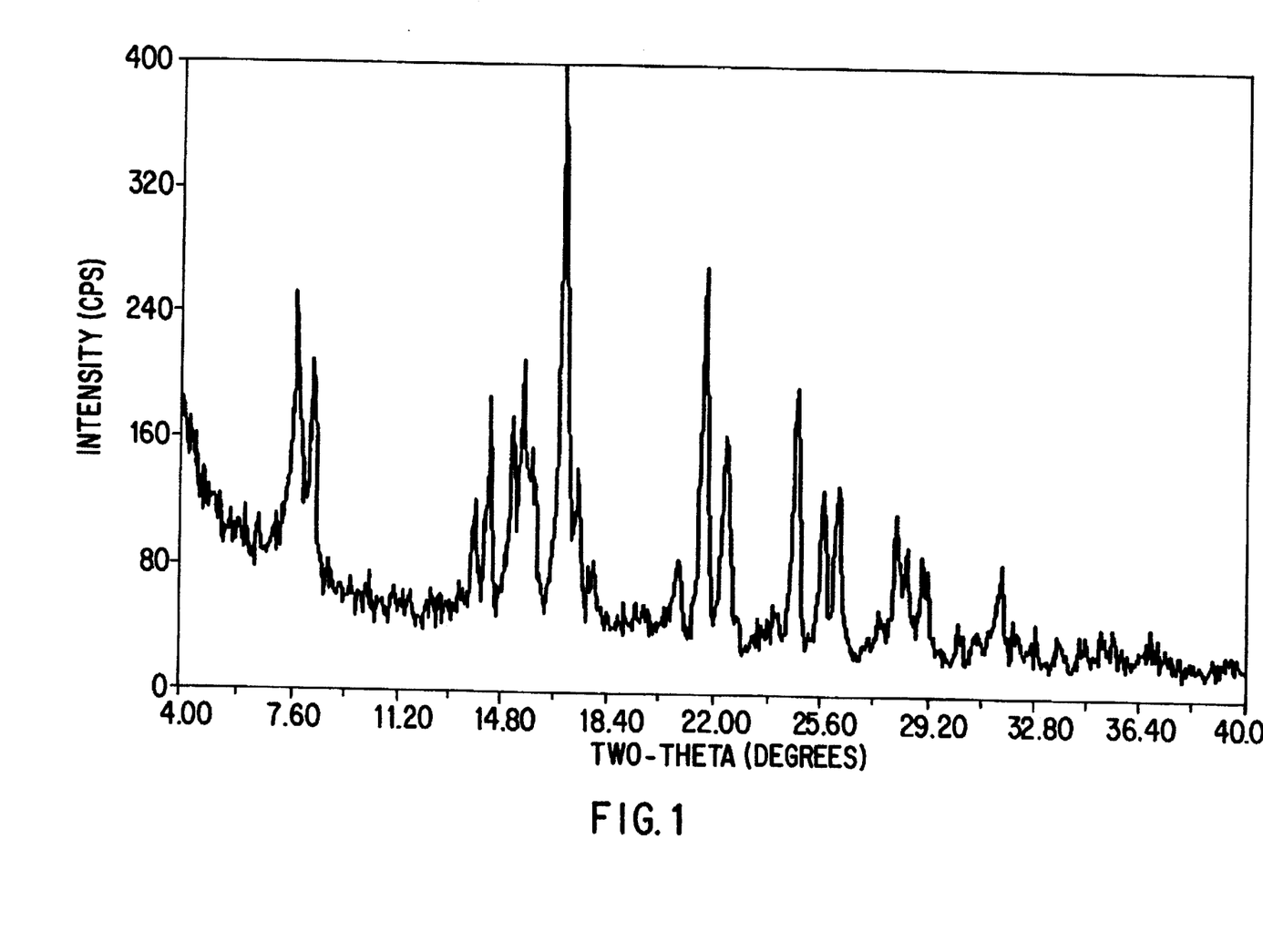
FIG. 1 is an X-Ray powder fraction pattern of ranitidine n HCl (n=1) (Form I) prepared by the method of the present invention.
Figure 2:
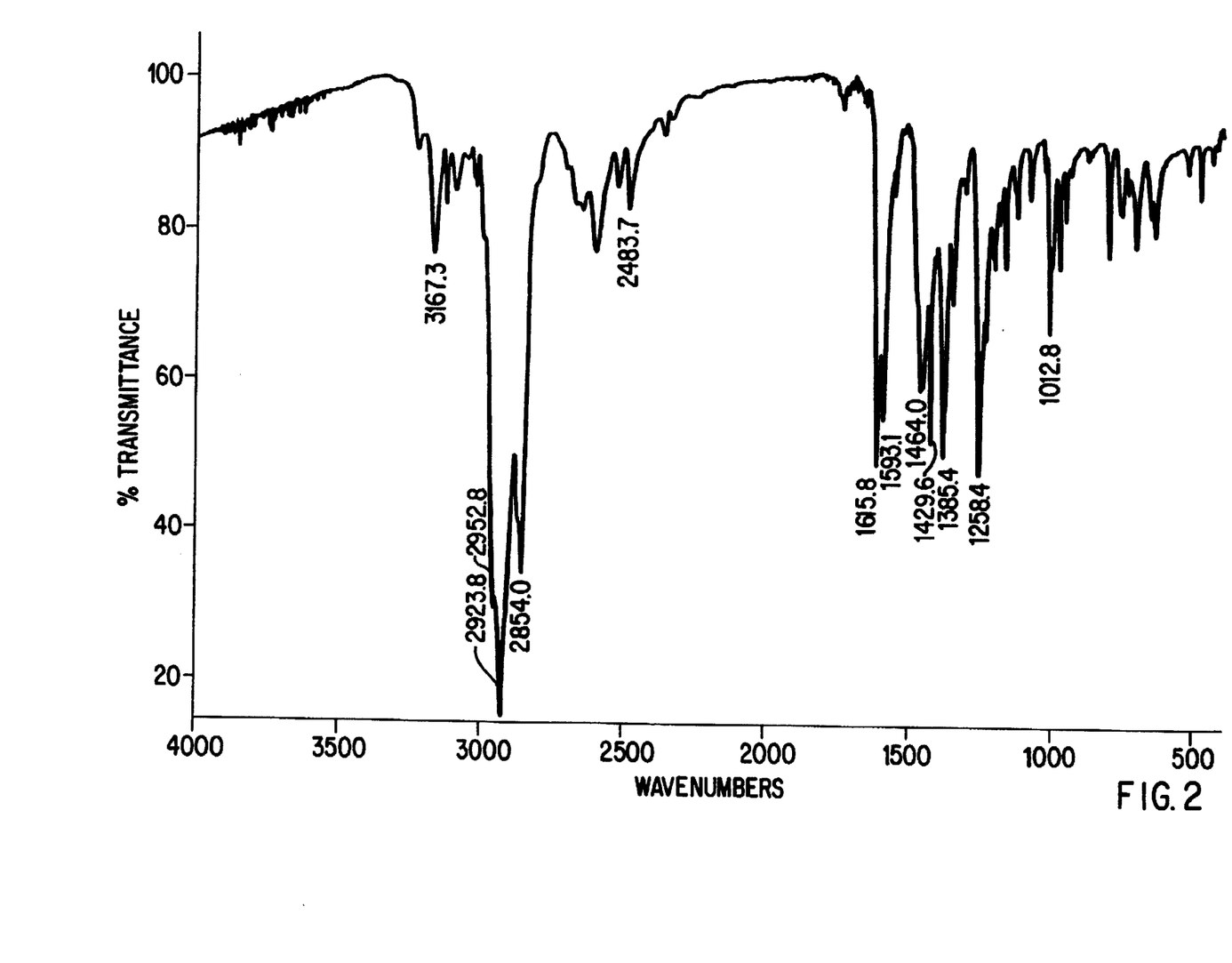
FIG. 2 an FT-IR spectrum of ranitidine n HCl (n=1) (Form I) prepared by the method of the present invention.

Analytical profiles of the ranitidine hydrochloride product of this reaction were obtained by X-Ray powder diffraction (FIG. 1), FT-IR analysis (FIG. 2), and H-Nuclear Magnetic Resonance (H-NMR) (FIG. 3).

Figure 7:
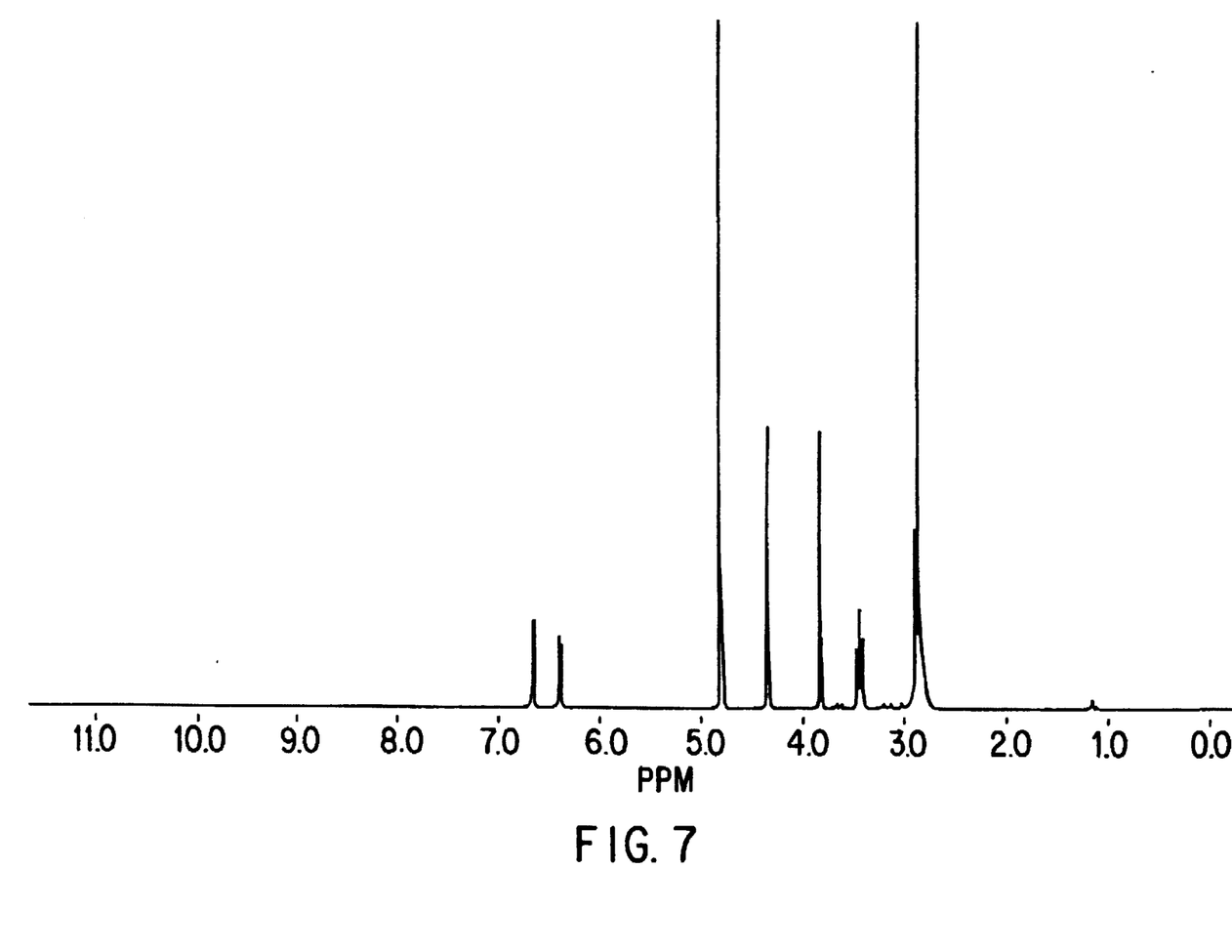
FIG. 7 is an H-NMR spectrum of ranitidine n HCl (n=1) prepared by the method of U.S. Pat. No. 4,128,658.

For comparative purposes, the H-NMR spectrum of ranitidine hydrochloride obtained by the method of U.S. Pat. No. 4,128,658 was obtained in the same manner as above and is shown in FIG. 7. It is believed that the two peaks between about 3.9 and about 3.5 PPM and two peaks between about 3.4 and about 2.9 PPM in the H-NMR spectrum are due to the uncontrolled reaction wherein more than one mole of hydrogen chloride was reacted per free amine.

EXAMPLE 2

Preparation of Form I ranitidine hydrochloride

Ranitidine free base (6.28 g (0.02 mol), pKa 2.3, 8.2) was charged in 120 ml of a mixture of a low polarity solvent system containing 60 ml anhydrous tetrahydrofuran and 60 ml anhydrous ethylacetate. 3.02 g (0.021 mol) of 2,5-dimethyl pyridine hydrochloride (pKa 6.43) was added to the reaction mixture with stirring and under protection from atmospheric moisture. Ranitidine hydrochloride was allowed to crystallize with stirring. The crystals were filtered off, washed with 40 ml of a mixture of tetrahydrofuran (20 ml) and ethylacetate (20 ml) and dried at 50° C. under reduced pressure to give 6.3 g of pure Form I ranitidine hydrochloride which was free from Form II rantidine hydrochloride and ranitidine n HCl (n>1) and other impurities.

EXAMPLE 3

Preparation of Form I ranitidine hydrochloride

Ranitidine free base (6.28 g (0.02 mol)) was charged in 120 ml of a mixture of a low polarity solvent system containing 60 ml of anhydrous tetrahydrofuran and 60 ml of axthydrous ethylether. 3.02 g (0.021 mol) of 2,5-dimethyl pyridine hydrochloride was added to the reaction mixture with stirring and under protection from atmospheric moisture. Ranitidine hydrochloride was allowed to crystallize at room temperature with stirring. The crystals were filtered off and washed with 40 ml of a mixture of tetrahydrofuran (20 ml) and ethyl ether (20 ml) and dried at 50° C. under reduced pressure to give 6.3 g pure Form I ranitidine hydrochloride, which was free from contamination with Form II or ranitidine n HCl (n>1) and other impurities.

EXAMPLE 4

Preparation of Form I ranitidine hydrochloride

Ranitidine free base (31.4 g (0.1 mol)) was charged in 200 ml of a mixture of a low polarity solvent system containing 160 ml anhydrous tetrahydrofuran and 40 ml ethyl alcohol. 15.8 g (0.11 mol) of 2,5-dimethyl pyridine hydrochloride was added to the reaction mixture with stirring and under protection from atmospheric moisture. Ranitidine hydrochloride was allowed to crystallize at room temperature with stirring. The crystals were filtered off and washed with 40 ml of a mixture of tetrahydrofuran (20 ml) and ethyl ether (20 ml) and dried at 50° C. under reduced pressure to give 30 g of pure Form I ranitidine hydrochloride, which was free from contamination with Form II, ranitidine n HCl (n>1) or other impurities.

EXAMPLE 5

Preparation of Form I ranitidine hydrochloride

Ranitidine free base (6.28 g (0.02 mol)) was charged in 100 ml of anhydrous tetrahydrofuran. 3.02 g (0.021) of 2,5-dimethyl pyridine hydrochloride was added to the reaction mixture with stirring and under protection from atmospheric moisture. Ranitidine hydrochloride was allowed to crystallize at room temperature with stirring. The crystals were filtered off and washed with 30 ml tetrahydrofuran and dried at 50° C. under reduced pressure to give 6.0 g of pure Form I ranitidine hydrochloride, which was free from contamination with Form II, ranitidine n HCl (n>1) and other impurities.

EXAMPLE 6

Preparation of Form I ranitidine hydrochloride

Ranitidine free base (50 g (0.16 mol) was dissolved in 500 ml of a mixture of industrial methylated spirit (250 ml, 74° o.p.) and ethylacetate (250 ml). 24.13 g (0.168 mol) of 2,5-dimethyl pyridine hydrochloride was added to the reaction mixture with stirring and under protection from atmospheric moisture. Ranitidine hydrochloride was allowed to crystalize with stirring. The crystals were filtered off, washed with a mixture of industrial methylated spirit (25 ml) and ethylacetate (25 ml) and dried at 50° C. under reduced pressure to give 50 g of Form I ranitidine hydrochloride, which was free from contamination from Form II, ranitidine hydrochloride n HCl (n>1), and other impurities.

EXAMPLE 7

Preparation of Form I ranitidine hydrochloride

Ranitidine free base (106 g (0.29 mol)) was charged in 130 ml of ethanol and diluted with 240 ml toluene under a constant flow of nitrogen. 40.5 g (0.35 ml) pyridine HCl in ethanol was added at ambient temperature. The reaction mixture was stirred until a suspension resulted, at which time it was diluted with 50 ml of a 1:1.5 mixture of ethanol/toluene. After stirring for one hour, 200 ml of isopropanol was added. The mixture was stirred for another hour and filtered. The filtrate was washed with 3×100 ml isopropanol and dried under vacuum at 50° C. to give 95 g (90%) of off-white product. IR analysis confirmed it to be pure Form I ranitidine hydrochloride.

EXAMPLE 8

Preparation of Form II ranitidine hydrochloride in the absence of water

Ranitidine free base (31.4 g (0.1 mol)) was dissolved in 300 ml of propan-2-ol at 40°–50° C. 12.7 g (0.11 mol) of 2,5-dimethylpyridine hydrochloride was added to the reaction with stirring. Ranitidine hydrochloride was allowed to crystallize at room temperature with stirring. The crystals were filtered off and dried at 50° C. under reduced pressure to give 32 g of pure Form II ranitidine hydrochloride, which was free from contamination from Form I, ranitidine n HCl (n>1) and other impurities.

EXAMPLE 9

Preparation of Form II ranitidine hydrochloride

Pyridine hydrochloride (2.6 g) was added to a solution of ranitidine (6 g) in 2-methylpropan-2-ol. The mixture was stirred at 40° C. to allow the product to crystallize and the resulting slurry was cooled to 20° C. The product was filtered off, washed with 2-methylpropan-2-ol and dried at 50° C. under reduced pressure to give Form II ranitidine hydrochloride (5.96 g) having a melting point of about 141°–142° C.

EXAMPLE 10

Preparation of Form II ranitidine hydrochloride

The process of Example 8 was repeated except that butan-2-ol was used in place of 2-methylpropan-2-ol and the mixture was stirred at 55° C. The resulting ranitidine hydrochloride was Form II and had a melting point of about 141°–142° C.

EXAMPLE 11

Preparation of Form II ranitidine hydrochloride

Ranitidine (6 g) was dissolved in industrial methylated spirits 74° o.p. (42 ml) at ambient temperature (about 20° C.). 2.6 g of pyridine hydrochloride was added to the solution. The temperature of the solution rose to 27° C. and the mixture was seeded to induce crystallization. The product crystallized to give a thick slurry at about 25°–27° C. After 0.5 hour the slurry was cooled to 10°–12° C. for 0.5 hour. The product was filtered off, washed with industrial methylated spirits (5 ml) and dried at 50° C. under reduced pressure to give 5.4 g Form II ranitidine hydrochloride having a melting point of about 139°–140° C.

EXAMPLE 12

Purification of Form I ranitidine hydrochloride from a mixture containing more than one species of ranitidine hydrochloride Ranitidine free base (50 g (0.1 mol)) was dissolved in industrial methylated spirits (74° o.p. (200 ml)) containing 0.16–0.192 equivalents of hydrogen chloride. 2-propyl pyridine (5 g) was dissolved in the reaction mixture. Ethyl acetate (200 ml) was added slowly to the solution. The ranitidine hydrochloride crystallized and was filtered off, washed with a mixture of industrial methylated spirits 74° o.p. (50 ml) and ethyl acetate (50 ml) and was dried at 50° C. The product (50 g) was obtained as an off-white solid having a melting point of 133°–134° C.

EXAMPLE 13

Purification of Form II ranitidine hydrochloride in the absence of water from a mixture of ranitidine hydrochloride containing more than one species of ranitidine hydrochloride One equivalent (about 5.3 ml) of concentrated hydrochloric acid was added to a solution of ranitidine (20 g) in a mixture of propan-2-ol (300 ml) at 45° C. The mixture was heated to 50° C. and then 0.4 g pyridine was added to the reaction mixture. The resulting solution was stirred at 50° C. to allow the product to crystallize. The slurry was cooled to 10°–12° C. and the product was filtered off, washed with propan-2-ol (2×27 ml) and dried at 50° C. under reduced pressure to give 22 g Form II ranitidine hydrochloride having a melting point of 139°–141° C.

EXAMPLE 14

Purification of Form II ranitidine hydrochloride from a mixture containing more than one species of ranitidine hydrochloride Form II ranitidine hydrochloride (35 g) prepared by the method of U.S. Pat. No. 4,128,658 was warmed in a mixture of propan-2-ol (520 ml) and pyridine (0.2 g) and the resulting solution was stirred at 50° C. The product was allowed to crystallize at 50° C. The slurry was cooled to 10°–12° C. and the product was filtered off, washed with propan-2-ol (2×30 ml) and dried at 50° C. under reduced pressure to give Form II ranitidine hydrochloride (34 g) having a melting point of 139°–141° C.

EXAMPLE 15

Purification of Form II ranitidine hydrochloride from a mixture containing more than one species of ranitidine hydrochloride Form II ranitidine hydrochloride (50 g) prepared by the process of U.S. Pat. No. 4,128,658 and 0.3 g pyridine were dissolved in industrial methylated spirits 74° o.p. (200 ml) at 70° C. The solution was allowed to cool and the product crystallized out at 40° C. The resulting slurry was cooled to 0° C. and the product was filtered off, washed with industrial methylated spirits (20 ml) and dried at 50° C. under reduced pressure to give 47.7 g of Form II ranitidine hydrochloride having a melting point of 140°–142° C.

EXAMPLE 16

Purification of Form II ranitidine hydrochloride from a mixture containing more than one species of ranitidine hydrochloride Concentrated hydrochloric acid (HCl) (1.4 ml) was added to a solution of ranitidine (6 g) in 2-methylpropan-2-ol. The mixture was stirred at 40° C. to allow the product to crystallize and the resultant slurry was cooled to 20° C. Further concentrated HCl (about 0.2 ml) was added to the mixture and stirred for one hour at 20° C. 0.04 g pyridine was added to the reaction mixture. The product was filtered off, washed with 2-methylpropan-2-ol and dried at 50° C. under reduced pressure to give 5.96 g of Form II ranitidine hydrochloride having a melting point of 141°–142° C.

EXAMPLE 17

Purification of Form II ranitidine hydrochloride from a mixture containing more than one species of ranitidine hydrochloride The process of Example 12 was repeated except that butan-2-ol was used in place of 2-methyl-2-propan-2-ol and the mixture was stirred at 55° C. to give 6.1 g Form II ranitidine hydrochloride having a melting point of 140°–141° C.

EXAMPLE 18

Purification of Form II ranitidine hydrochloride from a mixture containing more than one species of ranitidine hydrochloride Ranitidine free base (6 g) was dissolved in industrial methylated spirits 74° o.p. (42 ml) at ambient temperature (about 20° C.). One equivalent (about 1.6 ml) concentrated HCl was added to the solution. The temperature rose to about 27° C. and 0.3 g pyridine was added to the reaction mixture. The solution was seeded to induce crystallization. The product crystallized to give a thick slurry at 25°–27° C. After 0.5 hour the slurry was cooled to 10°–12° C. for 0.5 hour. The product was filtered off, washed with industrial methylated spirits (5 ml) and dried at 50° C. under reduced pressure to give 5.4 g Form II ranitidine hydrochloride having a melting point of 139°–140° C.

EXAMPLE 19

Preparation of omeprazole (5-Methoxy-[[(a-methoxy-3,5-dimethyl-2-pyridinyl)methyl]sulfinyl]-1H-benzimidazole) monoacid salt Pure mono-acid salt of omeprazole free from contamination by the di-acid salt of omeprazole and other impurities is prepared by the stoichiometric acid transfer reaction using one mole of 2,5-dimethyl pyridine acid salt (pKa=6.3) to one mole of omeprazole free base (pKa 4.0 and 8.7) in a high polarity solvent, such as acetonitrile or hydroxylic solvent, or in a low polarity solvent, such as tetrahydrofuran. The mono-acid omeprazole crystals are allowed to form at room temperature with stirring. The crystals are filtered off and washed with sufficient amount of the solvent and dried at elevated temperature under reduced pressure to give pure omeprazole mono-acid.

EXAMPLE 20

Preparation of cefepime (7-[2-(2-aminothiazol-4-yl)-20(z)-methoximino acetmido]-3-[(1-methyl-1-pyrrolidino)methyl]-3-cephem-4-carboxylate acid salts Production of mono-acid salts from cefepime zwitterion The mono hydrochloride salt $(C_{19}H_{24}N_6O_5S_2.HCl.XH_2O)$ is prepared by the stoichiometric amine acid transfer reaction using one mole of pyridine hydrochloride to one mole of cefepime zwitterion in either a low polarity solvent system (water with acetone or 5% aqueous methanol) or a high polarity solvent system (methylene chloride).

The dihydrochloride salt $(C_{19}H_{24}N_6O_5S_2.2HCl.XH_2O)$ is prepared by the stoichiometric acid transfer reaction using two moles of 2-chloropyridine hydrochloride to one mole of cefepime zwitterion in either a low polarity solvent (water with acetone or 5% aqueous methanol) or a high polarity solvent (methylene chloride (80%) with methanol (20%)).

The half mole of sulfuric acid salt $[(C_{19}H_{24}N_6O_5S_2)_2.H_2SO_4]$ is prepared by the stoichiometric acid transfer reaction using one mole of pyridine sulfate $[(C_5H_5N)_2H_2SO_4]$ to two moles of cefepime zwitterion in either a low polarity solvent (water with acetone or 5% aqueous methanol) or a high polarity solvent (methylene chloride (80%) with methanol (20%).

The mono-sulfuric acid salt $(C_{19}H_{24}N_6O_5S_2.H_2SO_4)$ is prepared by the stoichiometric acid transfer reaction using one mole of 2-chloropyridine sulfate $[(C_5H_4NCl)_2.H_2SO_4]$ to one mole of cefepime zwitterion in either a low polarity solvent (water with acetone or 5% aqueous methanol) or a high polarity solvent (methylene chloride (80%) with methanol (20%)).

Crystallization, filtration, washing and drying of crystals is carried out as described in Example 7.

EXAMPLE 21

Preparation of the acid salts of the aminoglycoside class of antibiotic compounds The sulfuric acid salts equivalent to each pKa value of each aminoglycoside antibiotic compound listed below are prepared by the stoichiometric acid transfer reaction. Each of the aminoglcoside compounds contain five basic nitrogens.

Arbekacin n $H_2SO_4$
Betamycin n $H_2SO_4$

Gentamycin n H₂SO₄
Netilmycin n H₂SO₄
Paromomycin n H₂SO₄
Tobramycin n H₂SO₄

An organic amine sulfuric acid salt donor compound is reacted with the free base aminoglocoside antibiotic at the desired molar quantity of each reactant as described in Example 8. The high polarity solvent used for the reactions is ethanol; the low polarity solvent is chloroform. The value, n, in the resulting aminoglycoside antibiotic salt is 1, 1.5, 2 or 2.5.

EXAMPLE 22

Preparation of amine acid salts of various compounds

The desired crystalline size, shape and form of the following organic amine salt compounds are prepared by the stoichiometric acid transfer reaction in different polarity solvent systems as described in Example 7, using appropriate donor and donee compounds and suitable solvent.

2HCl or 1HCl salts of DN-9693: 7-(1-piperdinyl)-1,2,3,5-tetrahydroimidazo[2,1-b]quinasolin-2-one 2HCl or 1HCl salts of BMY 43351: 1-(cyclohexylmethyl)-4-[4-(2,3-dihydro-2-oxo-1H-imidazo[4,5-b]quinolin-7-yloxy)-1-oxobutyl]piperazine 4HCl or 2HCl salts of MDL 27,695: 1,19-Diphenyl-2,6,14,18-tetra-azanonadecane 6HCl or 3HCl salts of ukrain: 5,5',5"-[phosphinothiolidyne-tris(imino-2,1-ethanediyl-tris[5-methylchelidoninium] trihydroxide 8HBr or 2HBr salts of JM3100: 1,1'-[1,4-phenylenebis(methylene)]bis[1,4,8,11-tetra-azacyclotetra decane]

4HCl or 2HCl salts of BBE: trans-1,2-Bis(5-amidino-2-benzimidazolyl)ethene

2HCL or HCl salts of SK & F 1056895: N,N-Dimethyl-8,8-dipropyl-2-azaspiro[4,5]decane-2-propanomine (in a hydroxylic solvent)

2HCl or HCl salts of ametazole: 2-(pyrazol-3-yl)ethylamine

4H₂SO₄ or 2H₂SO₄ salts of framycetine

3HCl, 2HCl or HCl salts of liblomycin.

What is claimed is:

1. A method for preparing an acid salt of an amine compound which comprises placing a donor compound having at least one amine acid salt moiety in solution with a free amine compound, said donor compound having a pka below at least the highest pka of the free amine compound, to provide a transfer of acid salt moiety from the donor compound to the free amine compound, yielding as the product thereof an amine acid salt of the free amine compound.

2. The method of claim 1 wherein the acid moiety is transferred from the donor compound to the free amine compound in a stoichiometric reaction.

3. The method of claim 1 further comprising crystallizing the amine acid salt of the free amine.

4. The method of claim 3 further comprising the subsequent steps of isolating, washing and drying the product.

5. The method of claim 1 wherein the amine acid salt of the free amine consists essentially of a single species of amine acid salt compound.

6. The method of claim 1 wherein an approximately equimolar amount of each of the free amine compound and the donor compound are placed in solution to yield a monoacid salt of the free amine compound.

7. The method of claim 6 wherein the monoacid salt is ranitidine hydrochloride.

8. A method for preparing an acid salt of an amine compound which comprises placing an approximately equimolar amount of dimethylpyridine hydrochloride in solution with a free amine compound, said dimethylpyridine hydrochloride having a pKa below at least the highest pKa of the free amine compound, to provide a transfer of acid salt moiety from the dimethylpyridine hydrochloride to the free amine compound, yielding as the product thereof a monoacid salt of ranitidine hydrochloride.

9. The method of claim 6 wherein the monoacid salt of ranitidine hydrochloride is substantially free from ranitidine acid salt having more than one acid moiety per amine compound moiety.

10. The method of claim 9 wherein the monoacid salt of ranitidine hydrochloride is Form I which is substantially free from Form II ranitidine.

11. The method of claim 7 wherein the donor compound and the free amine compound are placed in solution in protic or aprotic solvent having low polarity.

12. The method of claim 1 wherein the donor compound has the general formula wherein R, R' and R" are each independently H, an aryl group having up to nine carbon atoms or an alkyl group having from one to twenty carbon atoms, or R, R' and R" together with N form a substituted or unsubstituted heterocyclic amine, is an amine compound and H-X is an acid moiety.

13. The method of claim 12 wherein the acid moiety is selected from the group consisting of HCl, H₂SO₄, HBr and H₃PO₄.

14. The method of claim 13 wherein the donor compound is selected from the group consisting of pyridine acid salt, dimethylpyridine acid salt, chloropyridine, quinoline acid salt and derivatives thereof.

15. The method of claim 1 wherein the amine acid salt of the free amine compound is an aminoglycoside acid salt antibiotic.

16. The method of claim 1 wherein the donor compound and the free amine compound are placed in solution in a protic or aprotic solvent having low polarity.

17. The method of claim 16 wherein the solvent comprises a mixture of organic solvents.

18. The method of claim 1 wherein the donor compound and the free amine compound are placed in solution in a protic or aprotic solvent having high polarity.

19. The method of claim 18 wherein the solvent comprises a mixture of organic solvents.

20. The method of claim 19 wherein the polarity of the mixture of solvents is adjusted to provide a desired polymorph of the product.

21. The method of claim 1 wherein the free amine compound and the donor compound are reacted at ambient temperature.

22. The method of claim 1 wherein the product is a monoacid salt of omeprazole, which is substantially free from di-acid salt of omeprazole.

23. The method of claim 1 wherein the free amine compound has two pKa values and the donor compound has a pKa value between the two pKa values of the free amine compound.

24. The method of claim 23 wherein the product is a monoacid salt of the free amine compound or a corresponding hydrate thereof.

25. The method of claim 1 wherein the free amine compound has two pKa values and the donor compound has a pKa value which is lower than the lower pKa value of the free amine compound.

26. The method of claim 25 wherein the product is a di-acid salt of the free amine compound or a corresponding hydrate thereof.

27. The method according to claim 1 wherein the free amine compound has three pKa values and the donor compound has a pKa value lower than the lowest pKa value of the free amine compound.

28. The method of claim 27 wherein the product is a tri-acid salt of the free amine compound or a corresponding hydrate thereof.

29. The method of claim 1 wherein the free amine compound has three pKa values and the donor compound has a pKa value between the highest pKa and second highest pKa value of the free amine compound.

30. The method of claim 29 wherein the product is a monoacid salt of the free amine compound or a corresponding hydrate thereof.

31. The method of claim 1 wherein the free amine compound has three pKa values and the donor compound has a pKa value between the second highest and the lowest pKa value of the free amine compound.

32. The method of claim 31 wherein the product is a monoacid of the free amine compound or a corresponding hydrate thereof.

33. A method for preparing Form I ranitidine n hydrochoride which is substantially free of Form II ranitidine hydrochloride comprising treating ranitidine free base with a donor compound capable of transferring HCl to the ranitidine free base in a solvent solution having a polarity suitable for precipitating the Form I ranitidine hydrochloride.

34. The method of claim 33 wherein the donor compound has a pKa in the range of from below about 8 to above about 3.

35. The method of claim 33 wherein the donor compound has a pKa of about 6.0 to about 6.6.

36. The method of claim 33 wherein the solvent is a protic or aprotic solvent having low polarity.

37. The method of claim 36 wherein the solvent comprises a mixture of anhydrous tetrahydrofuran and anhydrous ethylether at a 1:1 ratio (v/v).

38. A method for preparing form I ranitidine n hydrochloride which is substantially free of form II ranitidine n hydrochloride comprising treating ranitidine free base with a donor compound selected from the group consisting of pyridine HCl, dimethylpyridine HCl, chloropyridine HCl, quinoline HCl and derivatives thereof.

39. The method of claim 38 wherein the donor compound is 2,5-dimethylpyridine HCl.

40. The method of claim 39 wherein the ranitidine n hydrochloride is a monoacid salt which is substantially free of ranitidine n hydrochloride (n>1).

41. The method of claim 33 wherein the ranitidine n hydrochloride is an acid salt wherein n is greater than 1 and which is substantially free of monoacid salt of ranitidine hydrochloride.

42. A method for removing impurities from a mixture of an amine acid salt compound comprising more than one species of said amine acid salt compound comprising placing said mixture in solution with a free amine compound having a pKa value between two pKa values of the mixture of amine acid salt compound, to provide a selective transfer of acid salt moiety from the amine acid salt compounds comprising said mixture to the free amine to thereby remove impurities, yielding as the product thereof a single species of amine acid salt compound.

43. The method of claim 42 wherein the mixture comprises more than one species of ranitidine hydrochloride.

44. A method for removing impurities from a mixture of an amine acid salt compound comprising more than one species of ranitidine hydrochloride comprising placing said mixture in solution with pyridine having a pKa value between the two pKa values of the amino acid salt, to provide a selective transfer of acid moiety from the rantidine hydrochloride species to the pyridine to thereby remove impurities, yielding as a product thereof a single species of ranitidine hydrochloride.

45. The method of claim 43 wherein the mixture and the donor compound are placed in solution in protic or aprotic solvent having low polarity.

46. The method of claim 43 wherein the mixture and the donor compound are placed in solution in protic or aprotic solvent having high polarity.

* * * * *

UNITED STATES PATENT AND TRADEMARK OFFICE
CERTIFICATE OF CORRECTION

PATENT NO. : 5,686,588
DATED : November 11, 1997
INVENTOR(S) : Seo Hong Yoo

It is certified that error appears in the above-identified patent and that said Letters Patent is hereby corrected as shown below:

| Column | Line  |                                          |
|--------|-------|------------------------------------------|
| 6      | 11    | Do not indent formula.                   |
| 6      | 55    | Change "polymorphlc" to --polymorphic--. |
| 10     | 45    | Change "axthydrous" to --anhydrous--.    |
| 14     | 26+39 | Correct spacing.                         |

Signed and Sealed this

Twenty-second Day of September, 1998

Attest:

BRUCE LEHMAN

Attesting Officer        Commissioner of Patents and Trademarks